(12) United States Patent
Westermeyer

(10) Patent No.: US 11,752,012 B1
(45) Date of Patent: Sep. 12, 2023

(54) ARTHRODESIS SURGICAL APPARATUS AND METHOD

(71) Applicant: Travis Westermeyer, Encinitas, CA (US)

(72) Inventor: Travis Westermeyer, Encinitas, CA (US)

( * ) Notice: Subject to any disclaimer, the term of this patent is extended or adjusted under 35 U.S.C. 154(b) by 0 days.

(21) Appl. No.: 18/068,444

(22) Filed: Dec. 19, 2022

(51) Int. Cl.
| | |
|---|---|
| *A61B 17/16* | (2006.01) |
| *A61B 17/88* | (2006.01) |
| *A61B 17/84* | (2006.01) |
| *A61B 17/34* | (2006.01) |
| *A61F 2/46* | (2006.01) |
| *A61B 17/14* | (2006.01) |
| *A61B 17/15* | (2006.01) |
| *A61F 2/28* | (2006.01) |
| *A61F 2/30* | (2006.01) |

(52) U.S. Cl.
CPC .......... *A61F 2/4601* (2013.01); *A61B 17/147* (2016.11); *A61B 17/15* (2013.01); *A61F 2002/2835* (2013.01); *A61F 2002/30622* (2013.01); *A61F 2002/4687* (2013.01)

(58) Field of Classification Search
CPC ............ A61F 2002/2835; A61F 2/4601; A61F 2002/30622; A61F 2002/4687; A61B 17/1635; A61B 17/17147; A61B 17/15
See application file for complete search history.

(56) References Cited

U.S. PATENT DOCUMENTS

| | | | | |
|---|---|---|---|---|
| 4,696,308 | A * | 9/1987 | Meller | A61B 17/1668 73/864.45 |
| 5,197,967 | A * | 3/1993 | Wilson | A61B 17/1637 606/80 |
| 5,632,747 | A * | 5/1997 | Scarborough | A61F 2/4644 606/86 R |
| 5,895,426 | A * | 4/1999 | Scarborough | A61F 2/446 623/17.16 |
| 6,451,023 | B1 * | 9/2002 | Salazar | A61B 50/30 606/86 R |
| 8,221,423 | B2 * | 7/2012 | Gil | A61B 17/1635 606/180 |
| 11,026,702 | B2 * | 6/2021 | Westermeyer | A61B 17/848 |
| 2021/0121187 | A1 * | 4/2021 | Westermeyer | A61B 17/848 |

* cited by examiner

*Primary Examiner* — Zade Coley
(74) *Attorney, Agent, or Firm* — Lawrence Maxham

(57) ABSTRACT

Arthrodesis surgical methods and apparatus. After a guide pin is inserted into the joint to be fused, a core saw creates a cored-out cavity in the joint to be fixated. An autograft bone core is harvested with a core saw and is inserted into the cored-out cavity. The joint is then immobilized for the healing process.

10 Claims, 19 Drawing Sheets

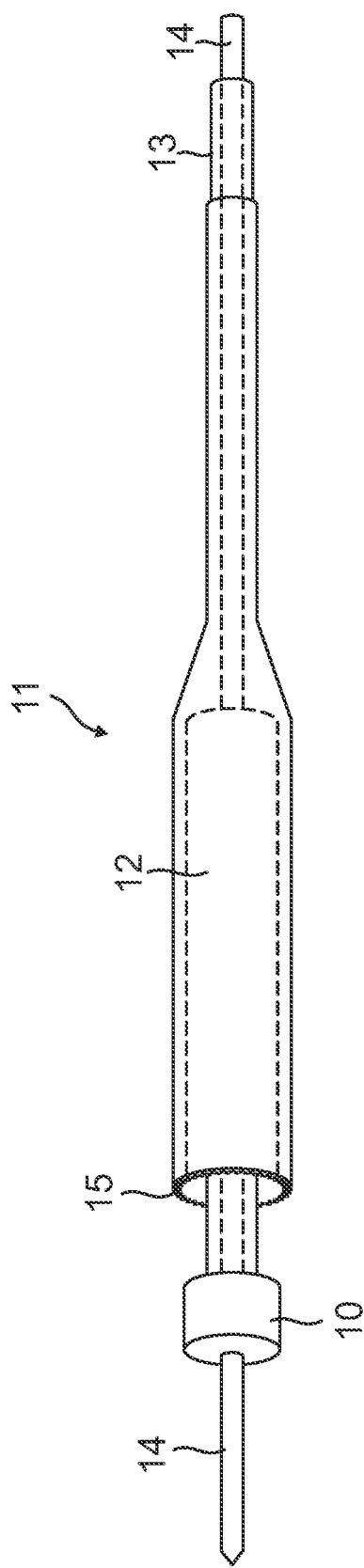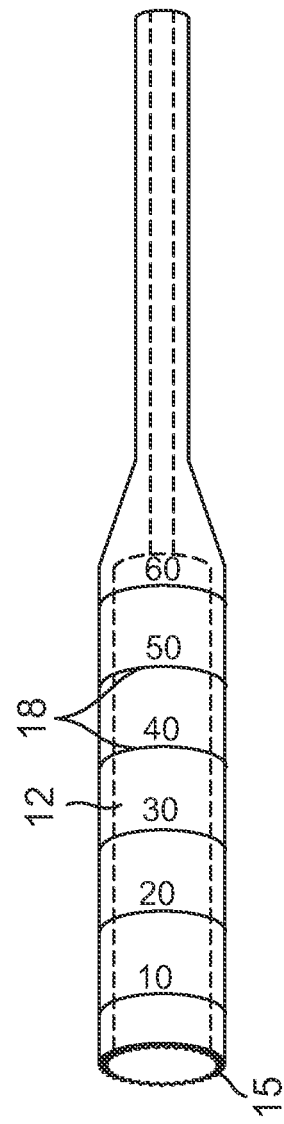
FIG. 1A
FIG. 1B
(PRIOR ART)

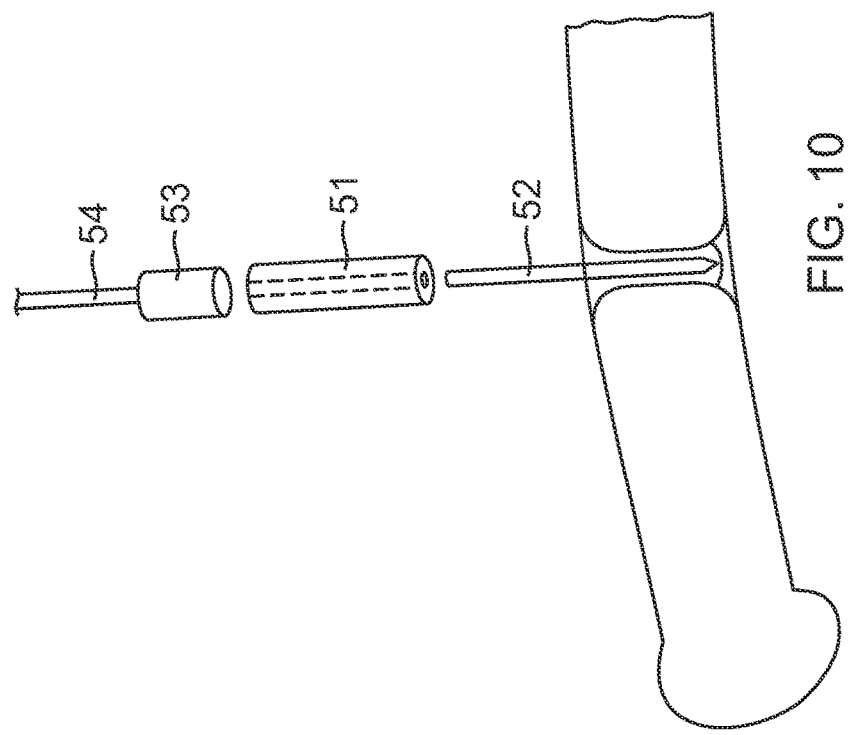
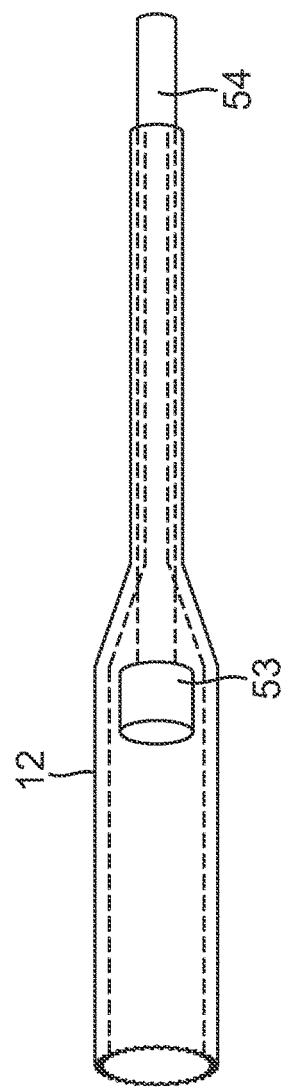
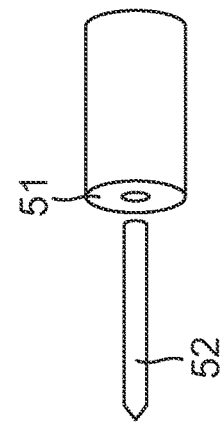
FIG. 10
FIG. 11

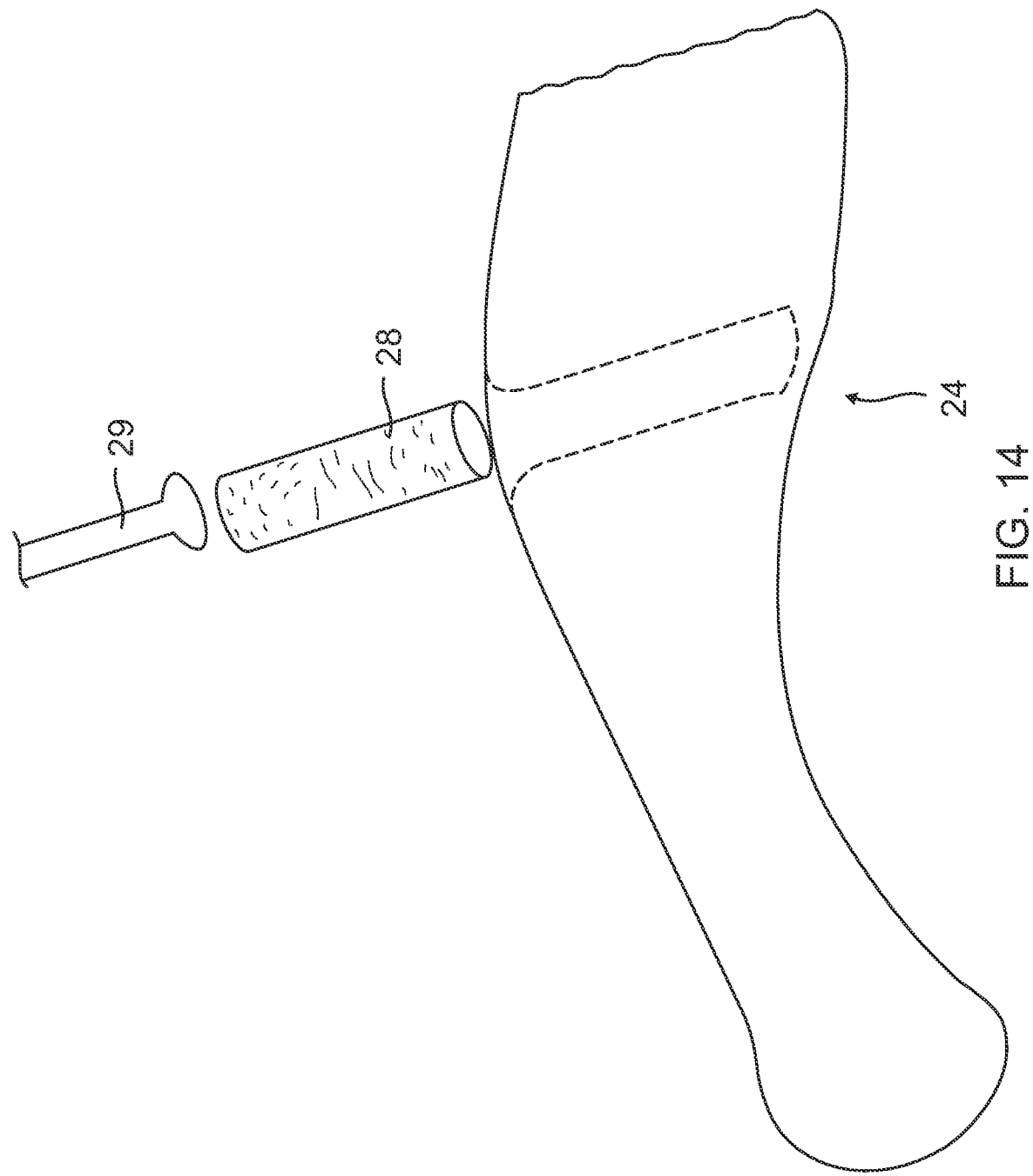

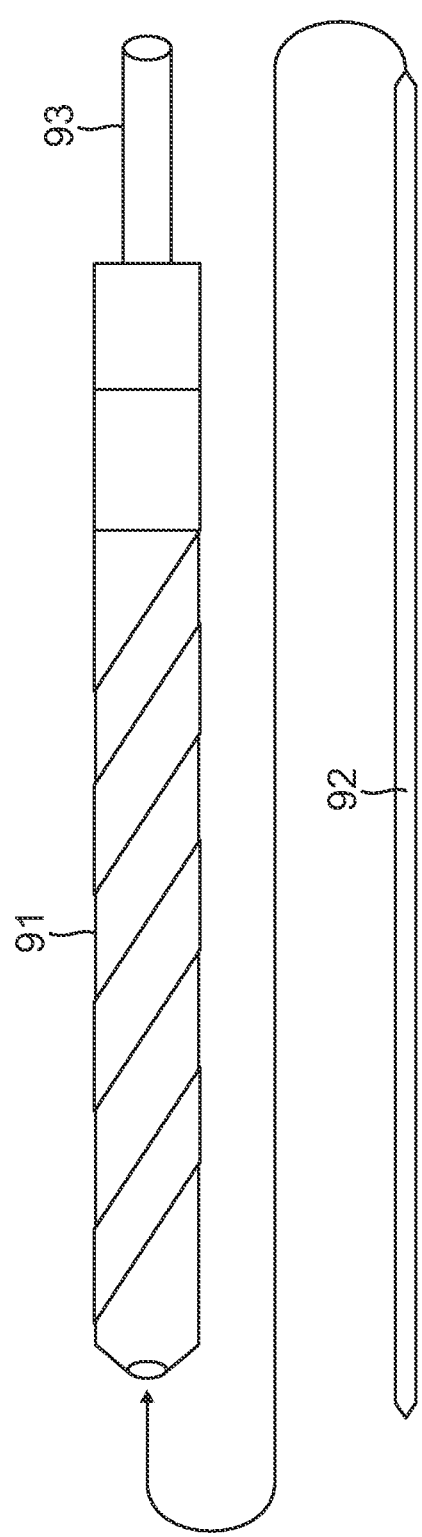
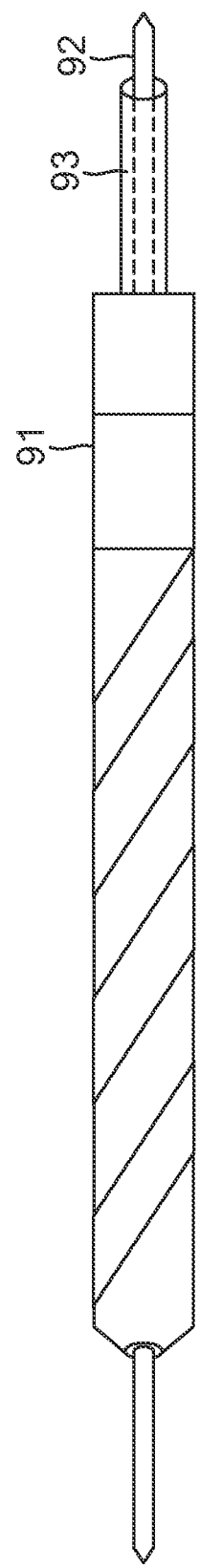
FIG. 19A
FIG. 19B

ARTHRODESIS SURGICAL APPARATUS AND METHOD

FIELD OF INVENTION

This apparatus relates to fusion of joints, and more particularly to a method and apparatus for simplifying and stabilizing the alignment of the adjacent bones in the joint and decreasing the time and effort required for the procedure, and for preventing the core saw from penetrating too deeply into the joint to be fused.

BACKGROUND OF THE INVENTION

Surgical immobilization of a joint by fusion of adjacent bones is a well-established procedure. Artificial induction of joint ossification between two bones by surgical means is employed to relieve intractable pain caused by one or more of several possible occurrences, including fractures, severe sprains, and arthritis.

Such procedures are most commonly performed on joints in the hand, ankle, foot, and spine.

According to one established procedure, metal implants can be attached to the two adjacent bones to hold them together in a position to enable permanent immobilization through bone growth, that is, by bone fusion. In some instances, damage of bones, for example, from arthritis, are removed on either side of a joint and the result is shortened metatarsals, carpals, or ankle joints, for example.

Arthrodesis procedures to accomplish bone fusion have presented challenges, starting from initial positioning of a core saw prior to coring out the bones to be fused, then maintaining the apparatus and bones to be fused in alignment and position as the procedure progresses.

These procedures have, in some instances, resulted in malunion and non-union problems.

SUMMARY

It is a purpose of this apparatus and method to alleviate the challenges identified above, among others. This is a greatly improved yet simplified apparatus and technique to correct simple as well as severe deformities, and fuse arthritic joints relatively easily and accurately. The apparatus not only improves the procedure of joint ossification and fusion, it includes a safety feature and guidance system to prevent from going too deep and keeps the core saw precisely in line and on target. This apparatus includes structure to prevent the core saw from coring out a hole that is equal to or greater than the thickness of the joint to be fused.

This arthrodesis surgical apparatus consists of reciprocal sizes of cannulated core saws, dedicated different sized plungers that go inside the cannulated saw, a guide, and alternatively, a depth gauge. The arthrodesis surgical apparatus has a very dramatic superior ability in preventing shortening, and streamlining, simplifying, and improving reproducible results, decreasing surgical procedure time, decreasing fusion patient healing time, and decreasing malunion/non-union problems. Arthrodesis significantly decreases the challenges of obtaining desirable orthopedic and biomechanical reduction of foot and ankle valgus and varus deformities, for example.

BRIEF DESCRIPTION OF THE DRAWING

The objects, advantages, and features of this concept will be more fully understood from the following detailed description, when read in conjunction with the accompanying drawing, in which:

FIG. 1A is a perspective view of a prior art apparatus related to the present invention;

FIG. 1B is a similar perspective view of the cannulated saw portion of the FIG. 1 apparatus, showing calibrations on the barrel portion of the saw;

FIG. 10 is a schematic representation of a second embodiment of the present invention showing the plunger, guide, and K-wire as separate devices;

FIG. 11 shows the elements of FIG. 10 in relation to the core saw;

FIG. 14 is a schematic representation of the final step in this method;

FIG. 19A is a side view of the drill bit and guide pin of a fifth embodiment of the present invention;

FIG. 19B is the FIG. 19A embodiment with the elements assembled;

DETAILED DESCRIPTION OF EMBODIMENTS OF THE INVENTION

Figure 2:
FIG. 2 is a side view of the guide pin of the FIG. 1 apparatus.
Figure 3:
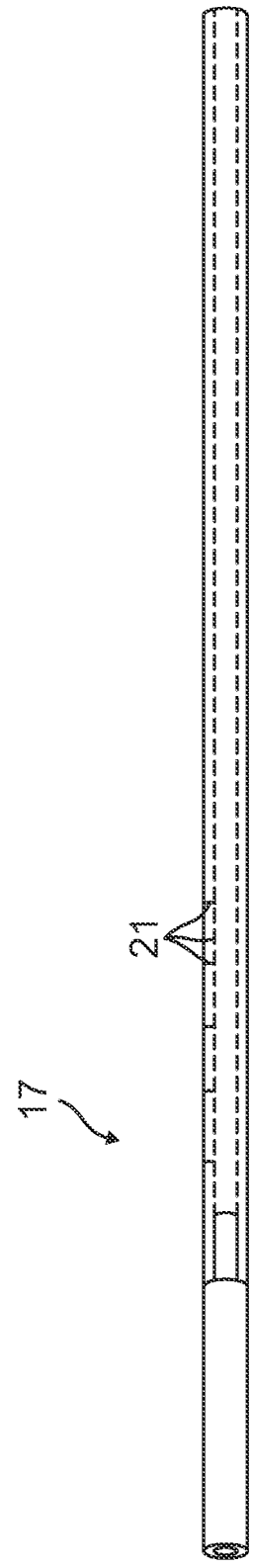
FIG. 3 is a perspective view of a cannulated depth gauge employed with the guide pin of FIG. 2.

With reference now to the prior art drawing figures, and more particularly to FIGS. 1-7, apparatus 11 includes core saw 12, through which extends cannulated plunger stem 13, through which extends guide pin 14. The core saw is comprised of a stem at its proximal end and a hollow barrel at its distal end.

The barrel of the core saw may have calibrations, as shown in FIG. 1B, at 10 mm, 20 mm, 30 mm, 40 mm, 50 mm, 60 mm, with 1 mm increments (not shown) between the marked numbered 10 mm-60 mm main calibration lines 18. The purpose of the calibrations on the core saw is to give the surgeon a reading as to how deep he is coring. This information will help the surgeon keep from coring too deep, past the other side of the bone, thereby enabling the surgeon to stop the advancement of the coring saw from going any deeper and thus avoiding any vital structures beyond the bone that is being cored out. The surgeon will get an idea how deep to core out the bone from the earlier reading he obtains from the depth gauge over the guide pin (FIG. 1A) in the initial steps of the fusion procedure.

When used, cannulated depth gauge 17 (FIG. 3) extends over guide pin 14 and is employed after the joint is X-rayed to determine proper positioning. This measurement is used to determine the proper depth of the hole to be formed in the adjacent bones and tissues of the joint to be fused. Calibration lines 21 are shown on the surface of the depth gauge to provide a measure of the proper depth and is used to create the autograft core, discussed below.

Figure 4:
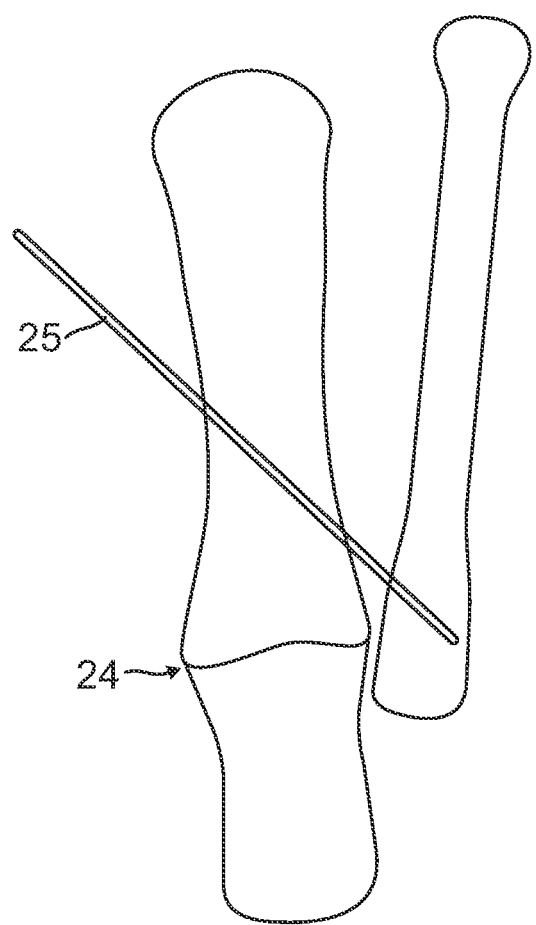
FIG. 4 is a schematic representation of the first step in an arthrodesis surgical procedure, using the apparatus of FIG. 1.
Figure 5:
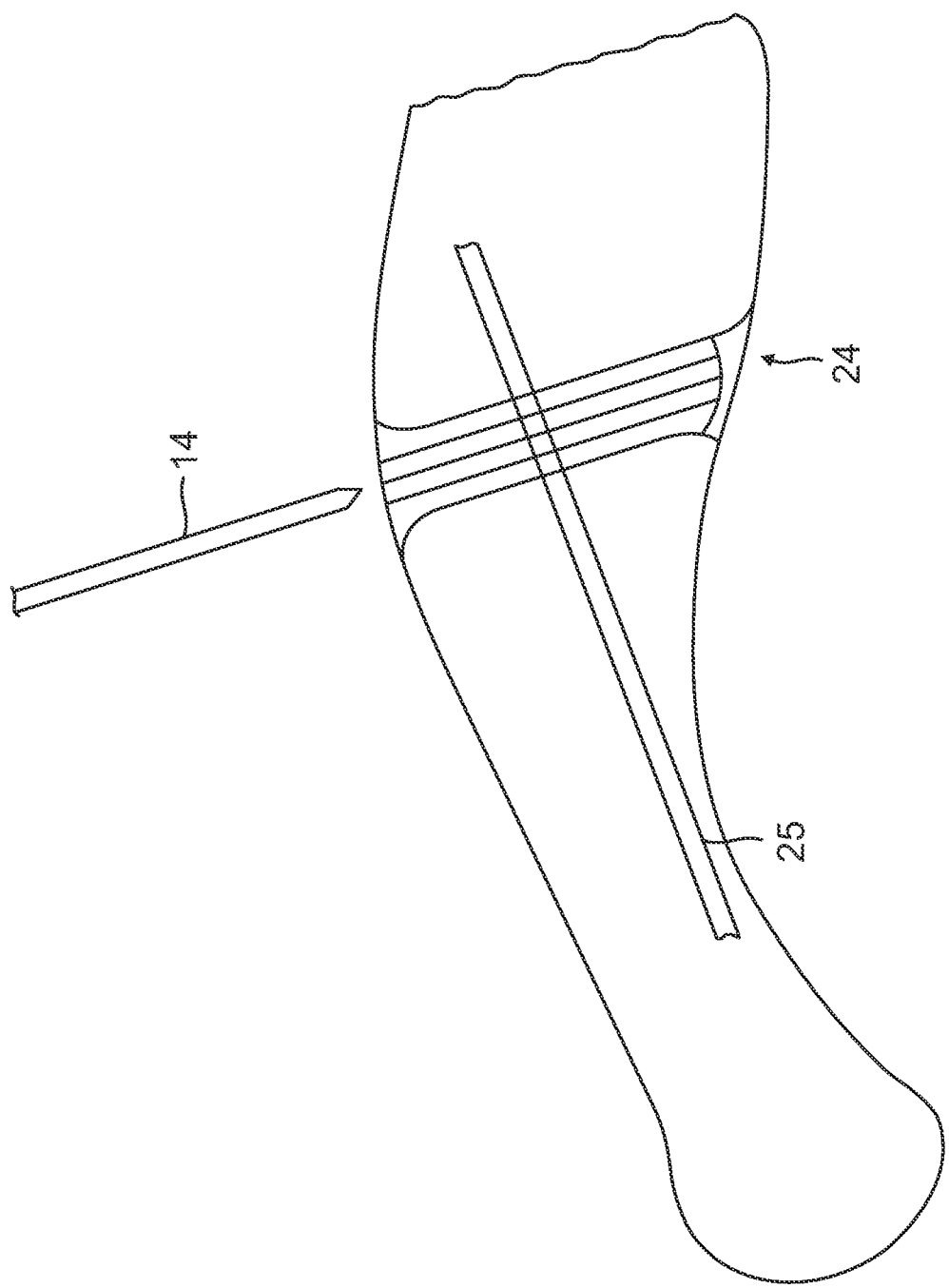
FIG. 5 is a schematic representation of the beginning of the second step in an arthrodesis procedure, using the apparatus of FIG. 1.
Figure 6:
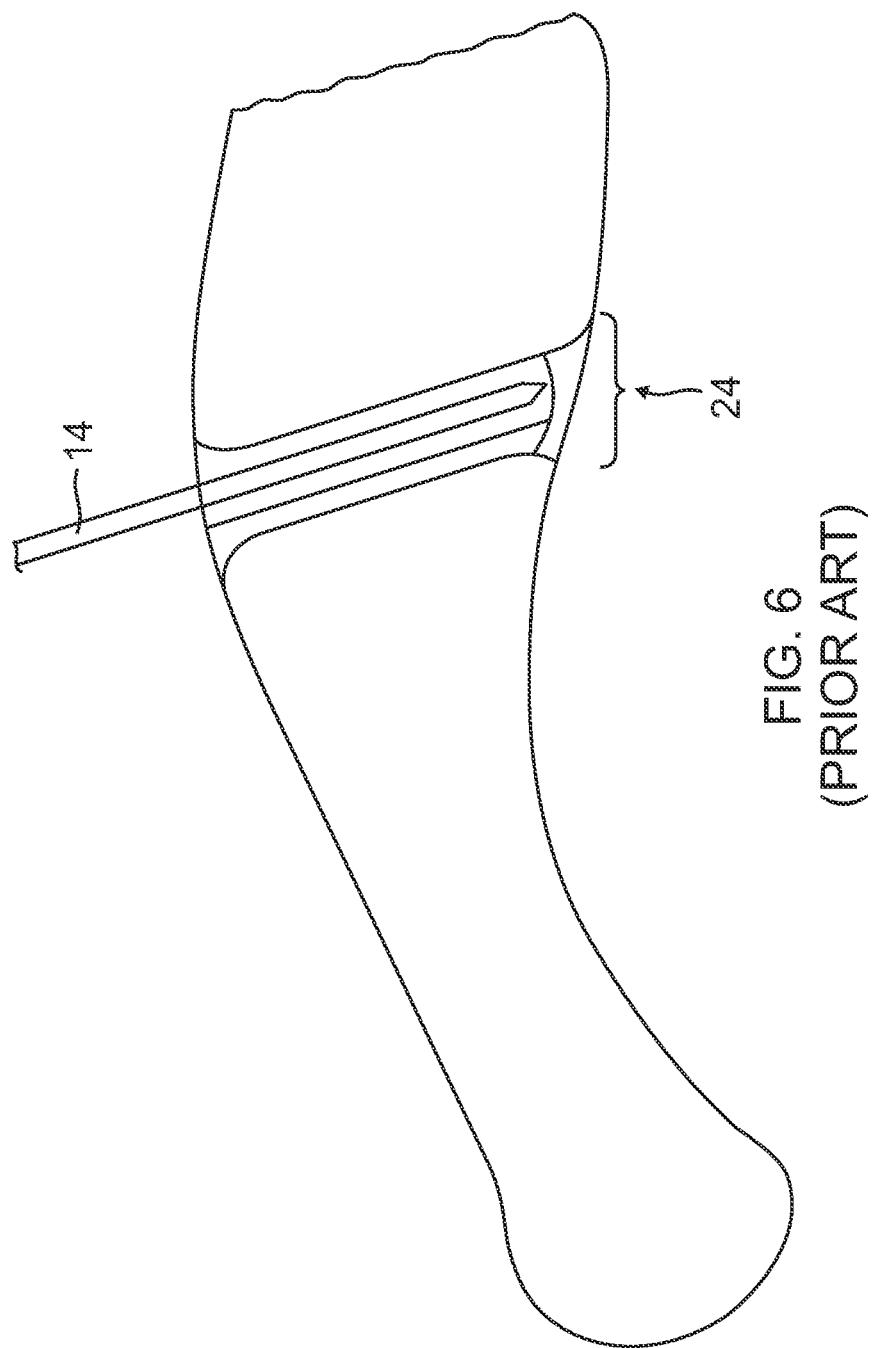
FIG. 6 is a representation of the second step process from FIG. 5.

The technique involves first manipulating the joint into the desired orthopedic position and then inserting temporary K-wire (Kirschner) 25 into adjacent bone to stabilize the joint 24 to be fused (FIG. 4). The K-wire fixation assures final desired position and alignment of the bones prior to the arthrodesis surgical procedure. Guide pin 14 is then inserted into the joint (FIGS. 5 and 6). To insert the guide pin it may be fitted to a drill hand piece, typically part of a power drill, and it is bored into the joint to a position as shown in FIG. 6. X-rays are taken to make sure the pin and the joint elements are in the desired position. While the depth gauge is normally used, it is optional in the practice of this procedure.

Figure 7:
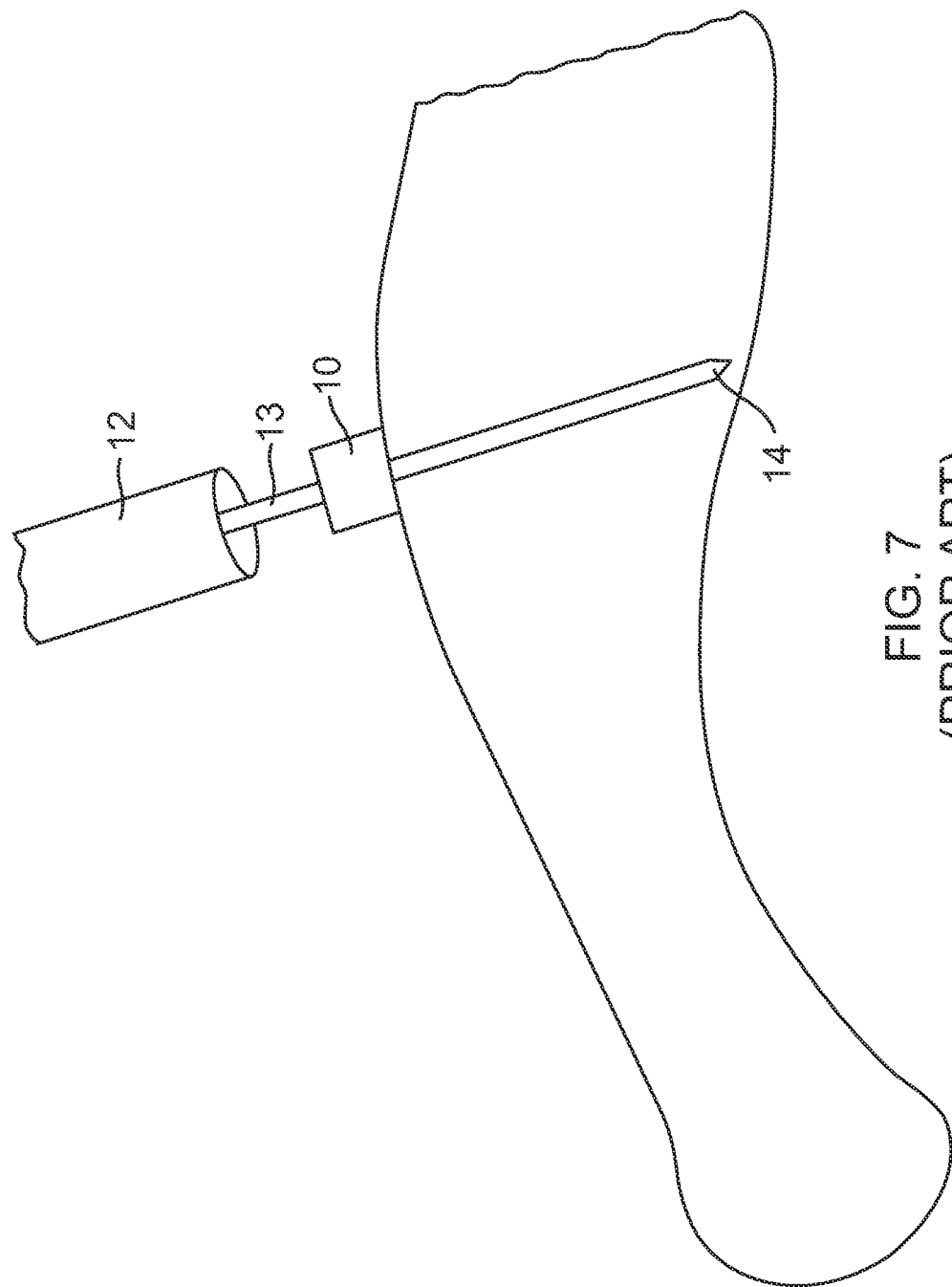
FIG. 7 is a schematic representation of the third step of arthrodesis procedure, using the apparatus of FIG. 1.

With reference to FIG. 7, cannulated plunger guide 10 on one end of plunger stem 13 is inserted into the desired size sawtooth (FIG. 1) distal end 15 of the barrel of cannulated core saw 12 which is loaded on a suitable powered drilling hand piece. The cannulated plunger is inserted over the guide pin and then the joint is cored out by teeth 15 using the powered drilling hand piece for rotation. When core saw 12 and guide 10 are removed, bone and cartilage material comprise a plug that is removed at the same time (see FIGS. 16 and 17).

Figure 8:
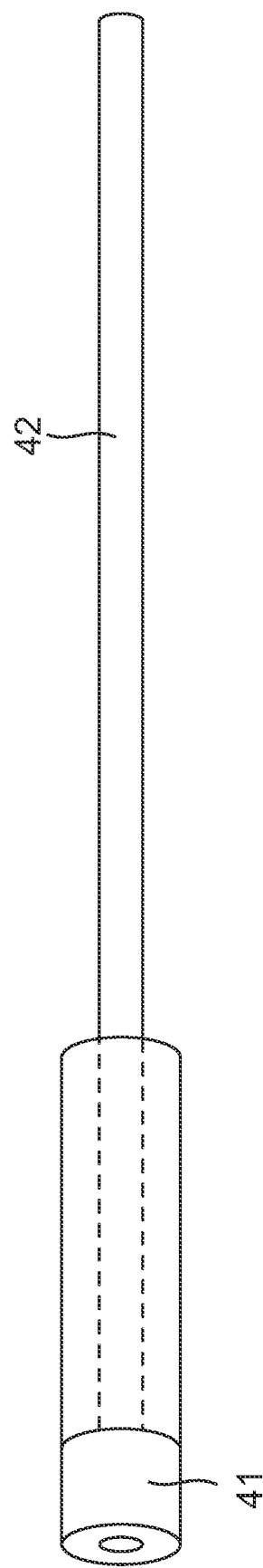
FIG. 8 shows the plunger guide on the end of the plunger stem as having different lengths, according to a first embodiment of the present invention.
Figure 9:
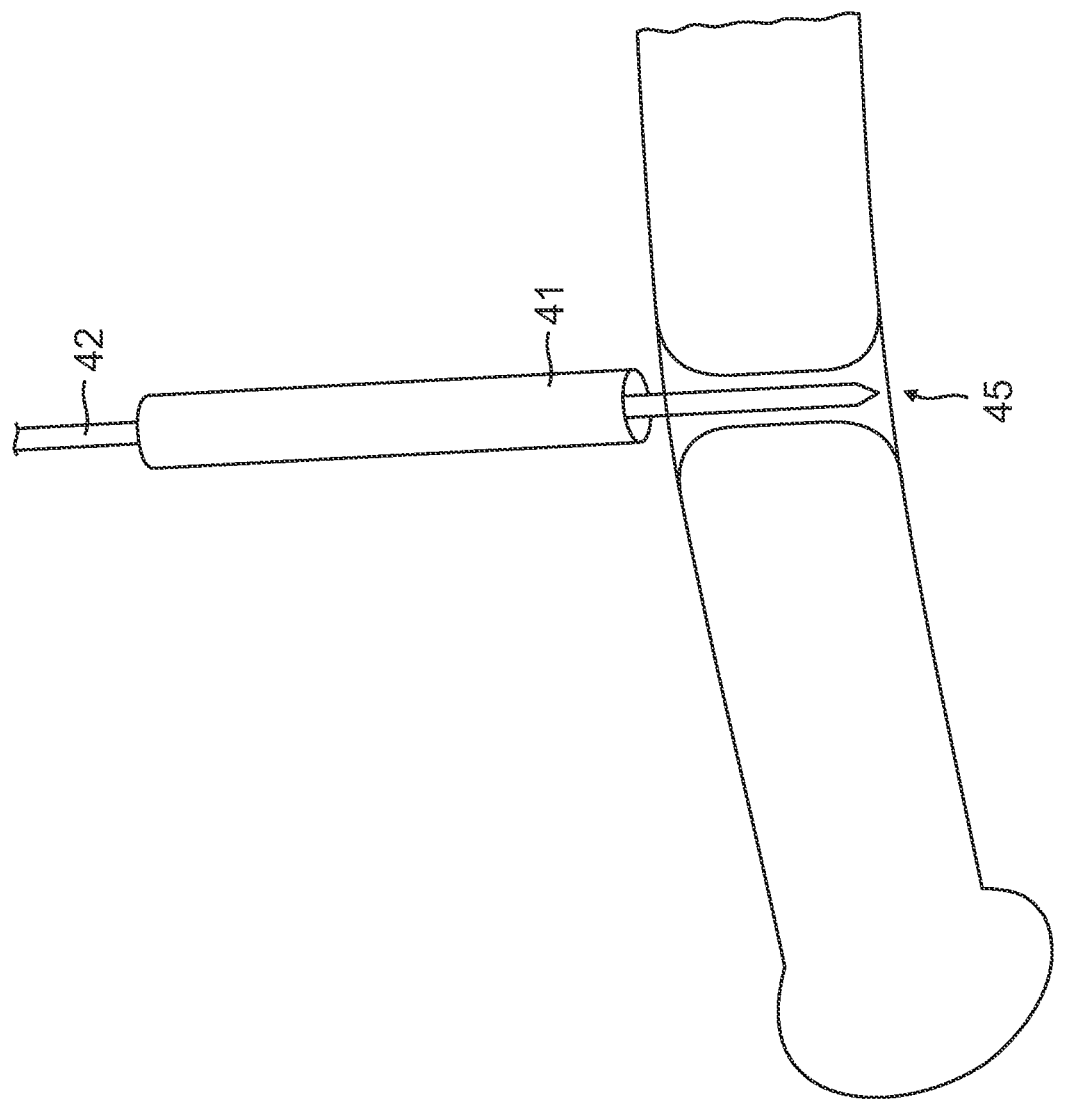
FIG. 9 shows a different embodiment of the present invention.

A first embodiment of the present invention is shown in FIGS. 8 and 9. In this embodiment, plunger guide 41 on the end of stem 42 has a length determined by the requirements of specific surgical procedure. In order to prevent the reaming core saw from creating a hole in the joint all the way through joint 45, the plunger guide is of a length to stop the core saw at a predetermined depth. For this purpose, plunger guide 41 may have a length ranging from 10 mm to 36 mm, for example. This length variability is represented by two pieces of guide 41. The plunger guide could be longer or shorter, but this range is sufficient for most arthrodesis procedures.

The FIGS. 8 and 9 embodiment functions in the same way as the apparatus shown in FIG. 1.

A second embodiment of the present invention is shown in FIGS. 10 and 11. Here guide 51, K-wire 52, and non-cannulated plunger 53 are separate elements. The plunger is affixed to the distal end of plunger stem 54. Guide 51 has different selectable lengths, as in the FIG. 8 apparatus.

The FIGS. 10 and 11 apparatus functions in the same manner as the prior embodiment.

Figure 12:
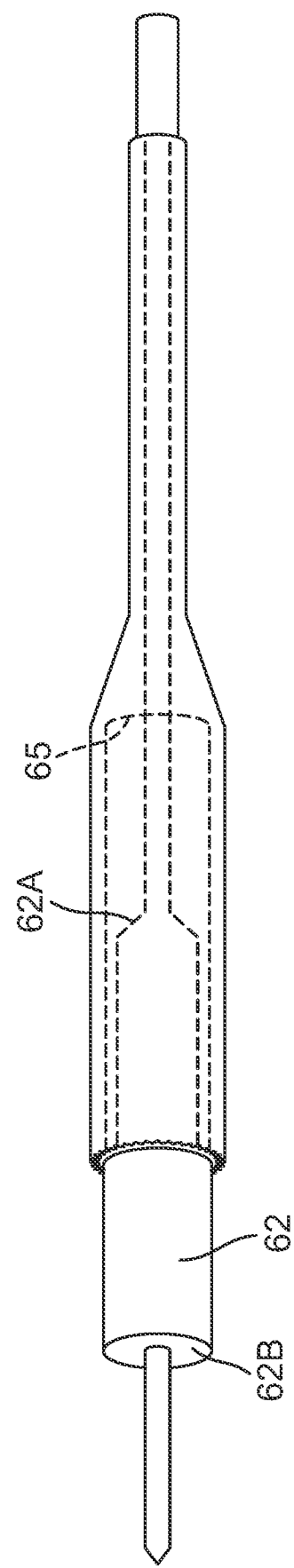
FIG. 12 is a perspective view of a third embodiment of the invention, the plunger, guide wire, and stem being unitary, showing the function of the guide in relation to the core saw just prior to starting the arthrodesis procedure.

FIG. 12 shows the unitary guide pin, guide, and plunger stem in relation to the core saw. This is a third embodiment. Here it can be seen how the proximal (inside) end 62A of guide 62 limits the depth of the core saw in reaming out the joint to be fused. The distal end 62B of the guide contacts the patient's bone at the hole being created at the outset of the arthrodesis procedure. As the saw cuts its way into the joint, the guide moves into the barrel of the core saw until end 62A contacts inside proximal end 65 of the core saw. At that point the coring out of the joint to be fused is concluded.

Figure 13B:
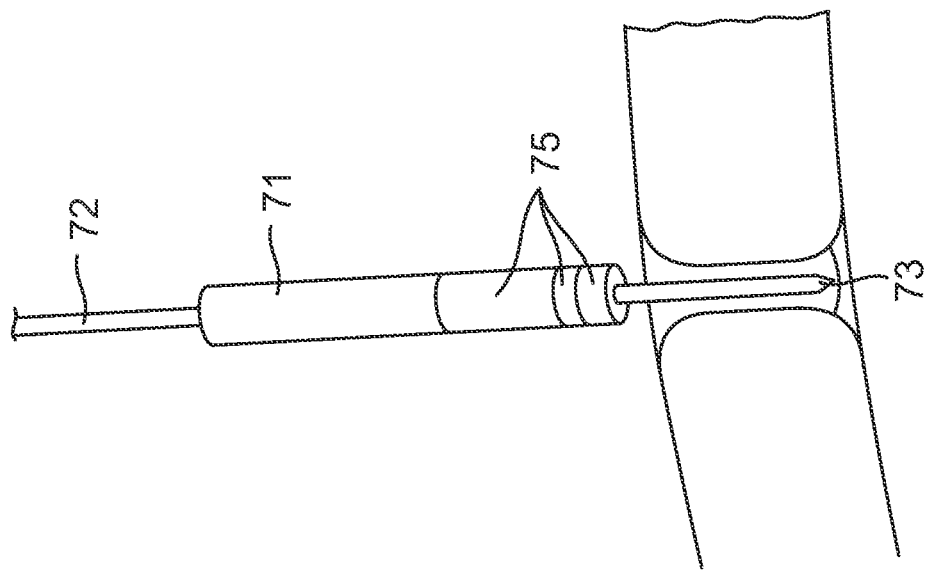
FIGS. 13A and 13B show a fourth embodiment of the guide in accordance with the present invention.
Figure 13A:
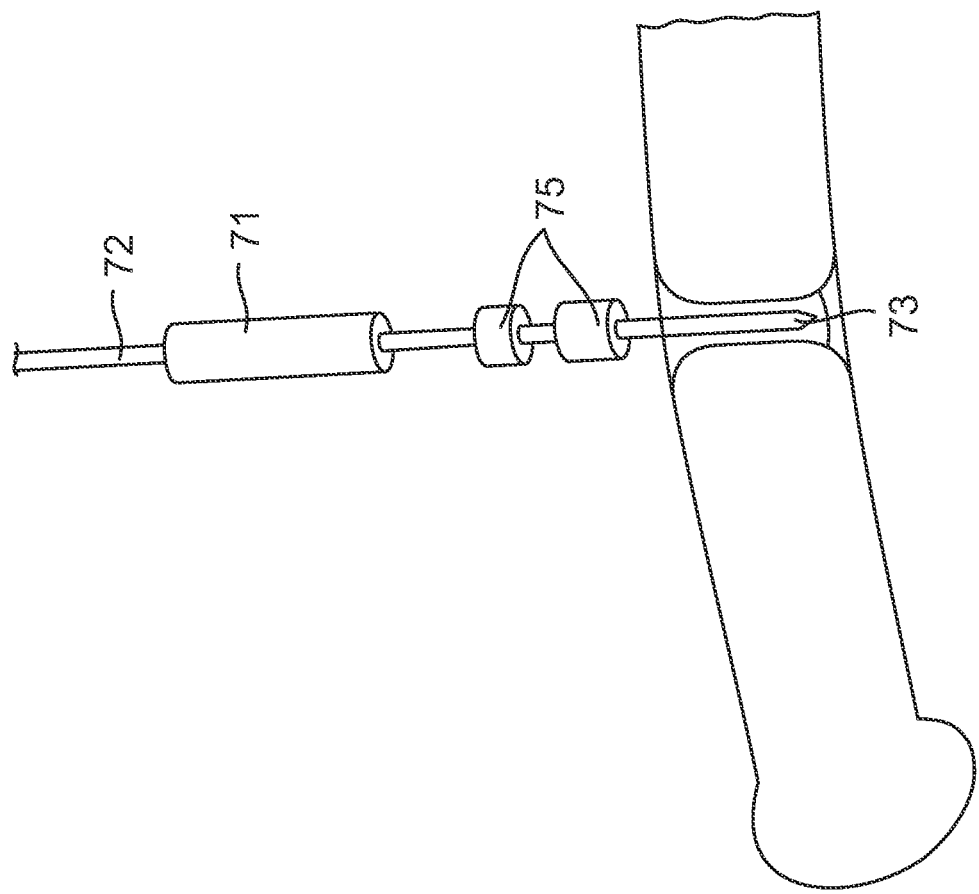
Figure 15:
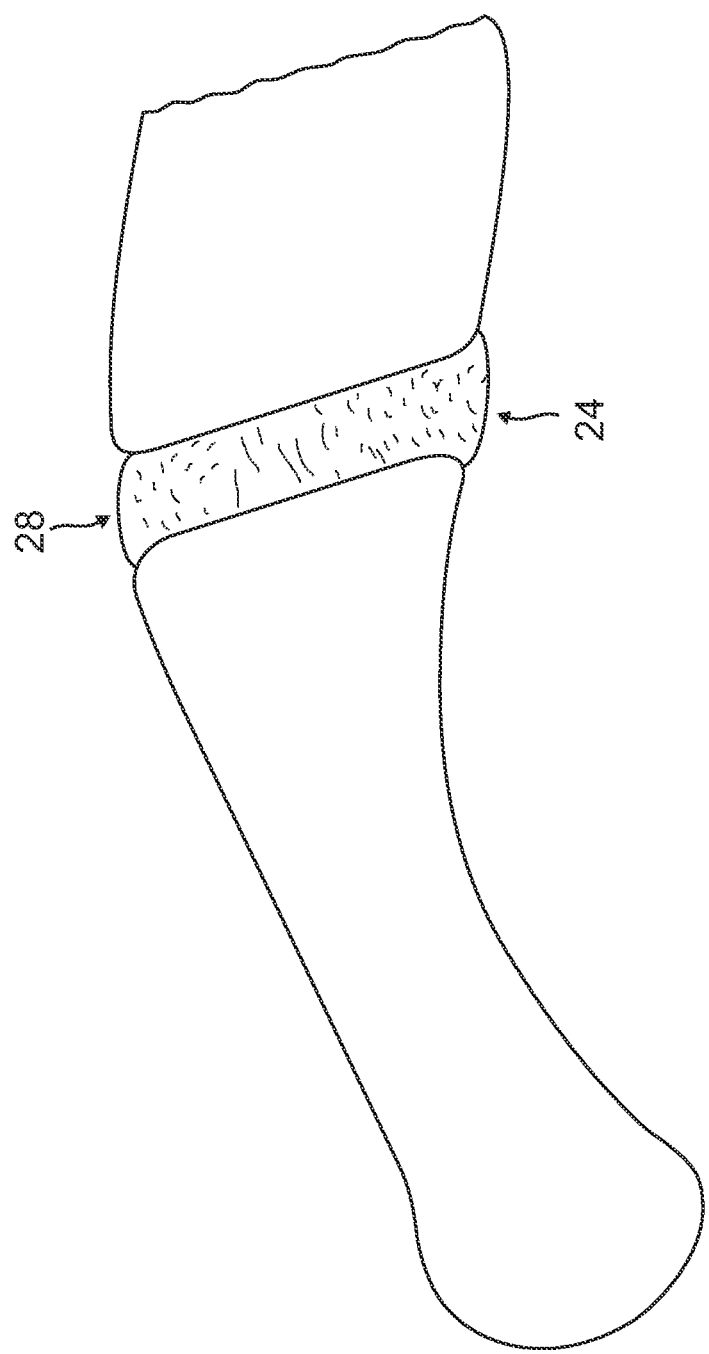
FIG. 15 shows the completion of this method.

A fourth embodiment of the present invention is shown in FIGS. 13A and 13B. In this embodiment, plunger guide 71 is mounted on the distal end of plunger stem 72, and guide pin 73 extends beyond the distal end of the guide. In order to have variable depth control, modular, cannulated shim guides 75 are used.

In keeping with the prior embodiments, the surgeon can use as many shim guides as necessary to achieve the depth control desired for the core saw. Each shim guide may have a length of 2 mm. Any number of shim guides can be used. It is contemplated that the maximum number would be 18, so the external guide would have a length ranging from 2 mm to 36 mm. Also, shim guides 75 are modular and could have lengths different from 2 mm.

Referring back to FIG. 9, the arthrodesis technique involves first manipulating the joint into the desired orthopedic position and then inserting Kirschner wire (K-wire) guide pin into the joint 45 to be fused. X-rays are taken to make sure the pin and the joint elements are in the desired position. The guide pin assures final desired position and alignment of the bones prior to the arthrodesis surgical procedure. Guide 41 is positioned within the drill bit which is typically part of a power drill.

After the joint elements are determined to be in the desired position, the reaming core saw is moved forward into position so that the distal end with cutting teeth is in position to core out bone and cartilage at the subject joint. At that point guide 41 is inside the distal end of the core saw. As the procedure progresses, the guide moves forth up into the hollow core saw and the plug of bone and cartilage material pushes the guide beyond the open end (see FIG. 16).

Further, as the diameter of the core saw varies to match the job to be done, so does the diameter of the guide so that it nearly matches the inside diameter of the core saw.

Figure 16:
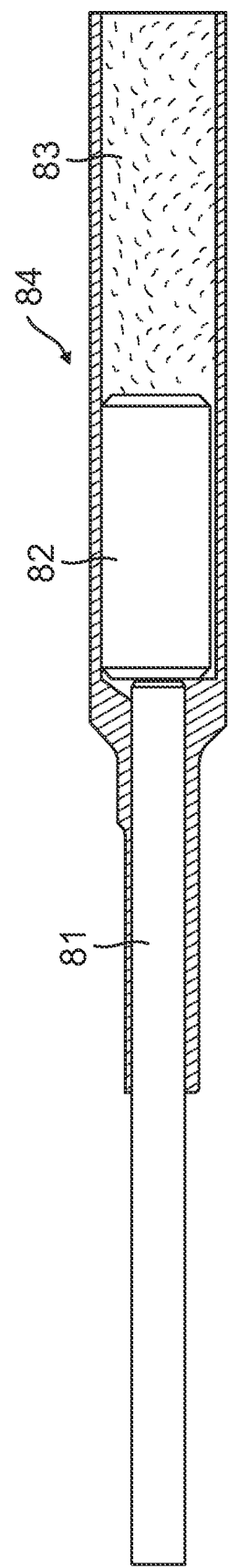
FIG. 16 is a graphical representation of the core saw barrel with the guide and the material from the patient therein.
Figure 17:
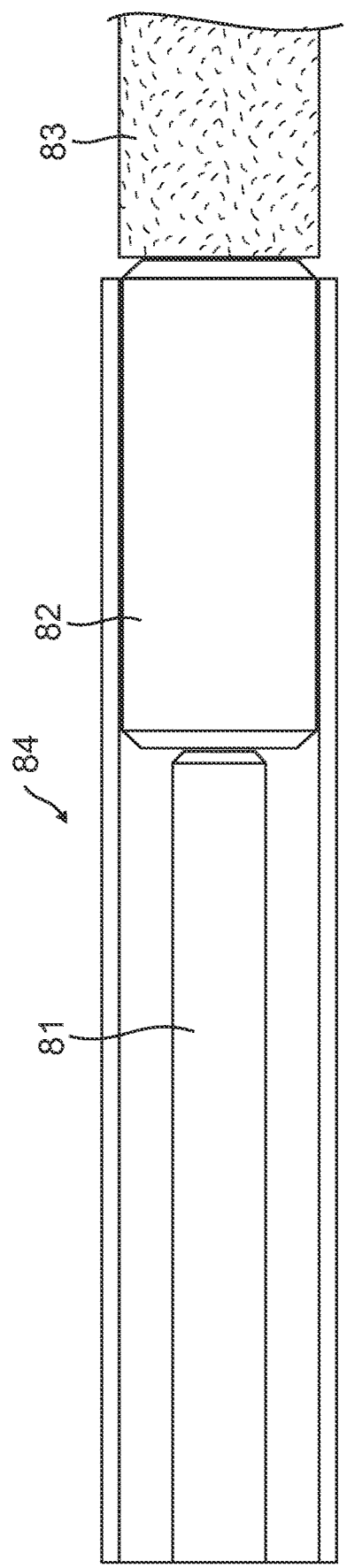
FIG. 17 shows the guide and bone material being pushed out of the core saw by the plunger.

Upon completion of the coring process, the core saw is removed, taking with it the debris, plunger, guide pin, and plunger stem (see FIGS. 16 and 17). The plunger stem 81 is then moved forward to push guide 82 through the cannulated core saw 84 to force out the bone and cartilage material 83 removed from the joint to be fused. A mallet may be used for this purpose.

If used, optional cannulated depth gauge 17 (FIG. 3) is used after the guide pin is placed to determine proper depth. The depth gauge measurement is used to determine the proper depth of the hole to be formed in the adjacent bones and tissues of the joint to be fused. Calibration lines 21 are shown on the surface of the depth gauge to provide a measure of the proper depth and can be used to create an autograft core. The depth gauge can be used with all the described embodiments and will coordinate with the calibrations on the core saw in FIG. 1.

Whichever size of the cored out deficit diameter is, a reciprocal larger harvesting core saw is used with the same guide and plunger technique to harvest an autograft core 28 (FIG. 14) from a suitable large volume bone, such as either the calcaneus or tibia of the patient. The inner diameter of the autograft core saw head will be about 0.15 mm larger than the diameter of the deficit at the fusion site. This is to enable there to be a slight press fitting of the harvested autograft core 28. The autograft of bone will need to be tapped into the fusion site gently with a known bone tamp tool 29, as shown in FIG. 14. Once this has been accomplished the surgeon will then immobilize/stabilize the fusion site with their hardware of choice, that is, cannulated screws or locking plate and screw construct. The autograft deficit site will typically be backfilled with the surgeon's allograft or biologic of choice.

The cannulated core saw sizes may vary approximately from about 3 mm to about 14 mm depending on the size of the joint to be fused. Saws may be much larger depending on the size of the joint.

Figure 18A:
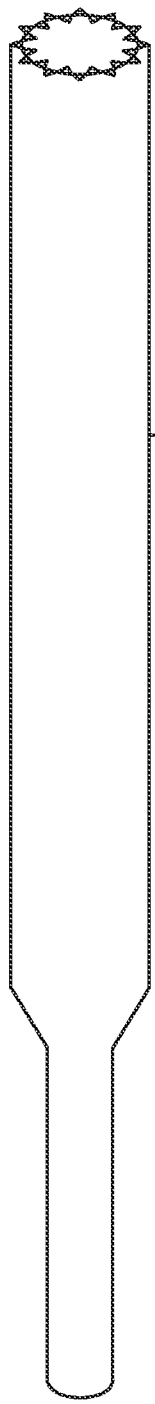
FIG. 18A is a perspective view of a core saw that is suitable for use with these embodiments.
Figure 18B:
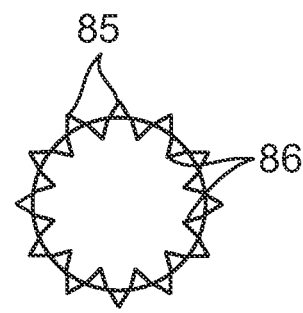
FIG. 18B is an enlarged end view of the cutting teeth arrangement of the core saw of FIG. 18.

An example of a core saw is shown in detail in FIGS. 18A and 18B. The hollow barrel of the core saw is identified as 84. The alternating cutting teeth are 85 and 86. The cutting end of the saw may initially be made with teeth that are all inline with the wall of the core saw barrel. Then they can be set so that outer teeth 85 and inner teeth 86 alternate to cant outwardly and inwardly, respectively. Or, the core saw can be initially manufactured with teeth 85 and 86 to be canted, as shown. The inward and outward cant of teeth 86 and 85, respectively, are shown somewhat exaggerated, for clarity.

This arrangement of the core saw teeth results in a clean cut through the bone and cartilage, with a slight clearance to remove the saw and the material as they are removed from the hole in the joint to be fused.

As mentioned above, the cannulated core saws will come in pairs. If the joint to be fused has a deficit of 10 mm, for example, then the cannulated core saw used to harvest the autograft will have an inner diameter of about 10.15 mm so that the autograft is slightly larger than the cored out fusion site. Likewise, if the fusion site is only a 6 mm diameter deficit, the inner diameter of the autograft cannulated core saw will be about 6.15 mm. Many different sizes can be created with this technique depending on how large the joint to be fused is. As an example, for fusing the first metatarsal phalangeal joint the core saw may be around 10 mm in diameter. For ankle or midfoot fusions, it may be smaller or larger in size. This also may have application for fusions of the hand, upper extremity, and even the spine.

An alternative, or fifth embodiment of the arthrodesis surgical apparatus of this invention is shown in FIGS. 19A-21.

The difference in this embodiment from the preceding embodiments is that instead of using the initial reaming core saw, this alternative embodiment uses a cannulated drill bit to ream out the joint. The procedure for reaming the joint is basically the same as in the prior embodiments except there is no plunger and the drill bit (not core saw) is guided with only a guide pin. The guide pin is generally a Kirschner wire that will vary in diameter size as the drill bit increases or decreases in diameter size.

Figure 20:
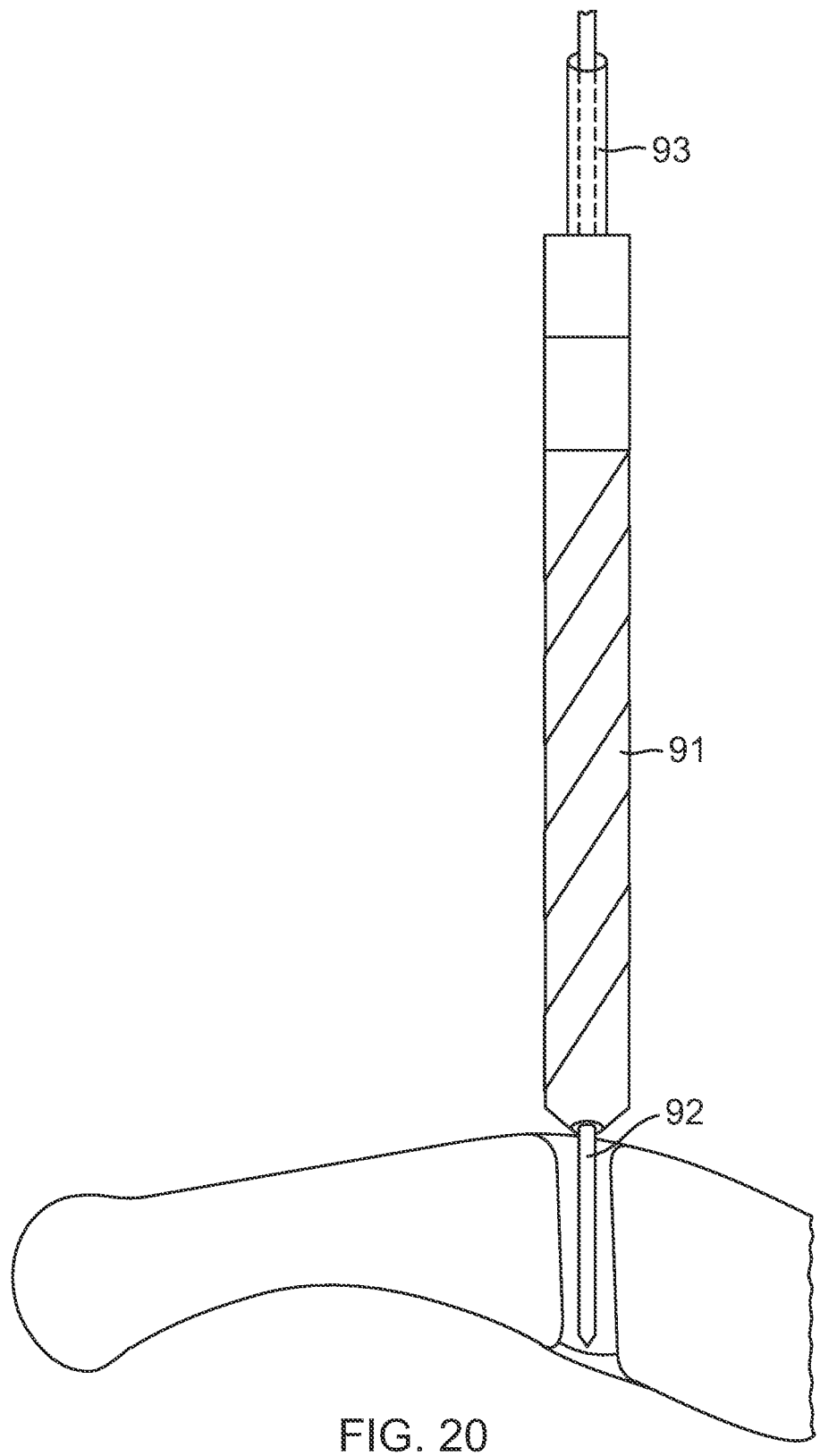
FIG. 20 is patterned after FIG. 6, showing the drill bit and guide pin in place just prior to reaming out the joint to be fused.
Figure 21:
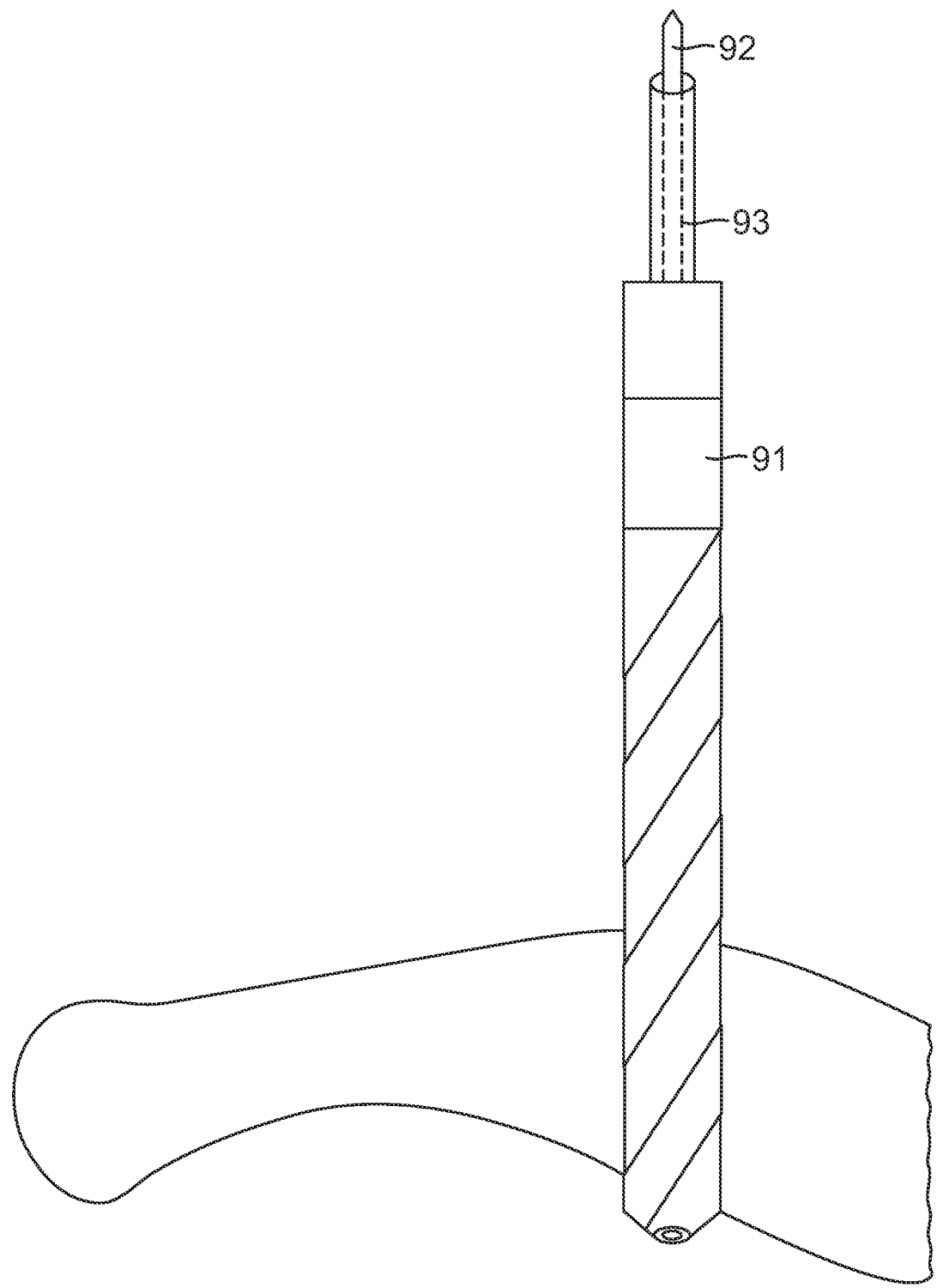
FIG. 21 shows the drill bit after reaming of the joint is completed.

FIG. 20 shows cannulated drill bit 91 and guide pin 92. Stem 93 is part of drill bit 91 and is cannulated, as is the entire drill bit.

This fifth embodiment is basically the same as the first embodiment except that the drill bit is reaming out the joint instead of using a core saw, and there is no plunger because there is no plug of bone and cartilage material to be removed from the drill.

Further, the core saw, guide pin, and plunger guide process to harvest the autograft and to install the autograft into the reamed out joint remain the same as in the foregoing embodiments.

Materials that the arthrodesis surgical device can be constructed of may vary depending on practicality of production and sales. PEKK (polyethyl ketone ketone) is very hearty, durable, and cost-effective material which would be practical for one-time usage. However, metal material would also work. PEEK (polyethyl ethyl ketone) may also be considered but it is a more expensive material.

What is claimed is:

1. Apparatus to facilitate fusion of bone joints, the apparatus comprising:
   an elongated, cannulated core saw device comprising a proximal end and a distal end, and having a hollow barrel with saw teeth at the distal end, said core saw barrel being hollow throughout its length;
   an elongated plunger which has a stem configured to extend through said core saw device, said plunger being sized to fit within the distal end of said core saw device;
   an elongated guide which is configured to extend within said core saw barrel and abut said plunger; and
   an elongated guide pin extending distally of said guide;
   said guide, guide pin, plunger, and core saw device being coaxial;
   after said guide pin is inserted into a joint to be fused, said guide is inserted over said guide pin, and said core saw device is inserted over said plunger and said core saw device is rotated to core out bone and cartilage material to form a core opening configured tea receive an autograft bone plug, said guide functioning to contact the bone of the joint to be fused and configured to limit the depth of said core saw device to less than the total thickness of the joint to be fused.

2. The apparatus of claim 1, and further comprising an elongated, cannulated depth gauge within which said guide pin extends.

3. The apparatus of claim 1, wherein said core saw device comprises two saw tooth heads, one size for creating the autograft plug and a smaller size head for creating the core opening in the joint to be fused.

4. The apparatus of claim 3, wherein the diameter difference of the saw tooth heads is about 0.15 mm.

5. The apparatus of claim 1, wherein the length of said guide is variable, depending upon the thickness of the joint to be fused.

6. The apparatus of claim 5, wherein said guide is comprised of at least two modular-length elements to enable its depth limiting function to be adjusted in relation to the thickness of the joint to be fused.

7. A method for facilitating bone joint fusion of a patient employing the apparatus of claim 1, comprising:
   inserting the elongated core saw device over the plunger, the core saw device having a first core saw head of a first diameter and a second core saw head of a second, larger diameter;
   rotating the first core saw head of the core saw device to remove bone and cartilage material to form a core opening in the joint to be fused, the guide limiting the depth of said core saw to less than the thickness of the joint to be fused;
   harvesting an autograft bone plug from the patient; and
   inserting the bone plug into the core opening.

8. The method of claim 7, and further comprising measuring the depth of the joint to be fused by means of a depth gauge inserted into the joint over the guide pin.

9. The method of claim 7, wherein the autograft bone plug is harvested using the second core saw head.

10. The method of claim 9, wherein said second core saw head is about 0.15 mm larger than said first core saw head.

\* \* \* \* \*